US011191285B2

(12) United States Patent
Lee et al.

(10) Patent No.: US 11,191,285 B2
(45) Date of Patent: Dec. 7, 2021

(54) ALLULOSE-CONTAINING COMPOSITION FOR PROMOTING EXCRETION OF VEGETABLE LIPIDS FROM THE BODY

(71) Applicants: CJ CHEILJEDANG CORPORATION, Seoul (KR); KYUNGPOOK NATIONAL UNIVERSITY INDUSTRY-ACADEMIC COOPERATION FOUNDATION, Daegu (KR)

(72) Inventors: Young Mi Lee, Suwon-si (KR); Seong Bo Kim, Seongnam-si (KR); Yang Hee Kim, Suwon-si (KR); Seong Jun Cho, Seoul (KR); Myung Sook Choi, Daegu (KR); Young Ji Han, Daegu (KR); Ji Young Choi, Daegu (KR); Su Jung Cho, Daegu (KR); Un Ju Jung, Busan (KR); Eun Young Kwon, Goyang-si (KR)

(73) Assignees: CJ CHEILJEDANG CORPORATION, Seoul (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 0 days.

(21) Appl. No.: 16/468,345

(22) PCT Filed: Dec. 26, 2017

(86) PCT No.: PCT/KR2017/015496
§ 371 (c)(1),
(2) Date: Jun. 11, 2019

(87) PCT Pub. No.: WO2018/124704
PCT Pub. Date: Jul. 5, 2018

(65) Prior Publication Data
US 2020/0170269 A1 Jun. 4, 2020

(30) Foreign Application Priority Data

Dec. 26, 2016 (KR) .................. 10-2016-0179487
Dec. 26, 2016 (KR) .................. 10-2016-0179488

(51) Int. Cl.
 *A23L 33/125* (2016.01)
 *A23D 7/005* (2006.01)
 *A61K 31/7004* (2006.01)
 *A23C 11/04* (2006.01)

(52) U.S. Cl.
 CPC ............ *A23C 11/04* (2013.01); *A23D 7/0053* (2013.01); *A23D 7/0056* (2013.01); *A23L 33/125* (2016.08); *A61K 31/7004* (2013.01); *A23V 2002/00* (2013.01)

(58) Field of Classification Search
 CPC ...... A61K 31/7004; A61P 3/06; A23L 33/125; A23L 33/30
 See application file for complete search history.

(56) References Cited

U.S. PATENT DOCUMENTS

| | | | | |
|---|---|---|---|---|
| 4,828,855 | A | * | 5/1989 | Sasaki ................ A23D 7/02 426/241 |
| 5,120,563 | A | * | 6/1992 | Mohlenkamp, Jr. ........ A23D 7/0053 426/601 |
| 2006/0247310 | A1 | | 11/2006 | Shinohara et al. |
| 2009/0304891 | A1 | | 12/2009 | Fujihara et al. |
| 2011/0166224 | A1 | | 7/2011 | Kishore et al. |
| 2015/0056360 | A1 | | 2/2015 | Beeson et al. |
| 2016/0302463 | A1 | | 10/2016 | Woodyer et al. |
| 2018/0179604 | A1 | | 6/2018 | Kim et al. |
| 2018/0243325 | A1 | | 8/2018 | Choi et al. |

FOREIGN PATENT DOCUMENTS

| | | |
|---|---|---|
| JP | 2008-222656 A | 9/2008 |
| JP | 2010-018528 A | 1/2010 |
| JP | 2015-512268 A | 4/2015 |
| JP | 2016-154463 A | 9/2016 |
| KR | 2009-0077072 A | 7/2009 |
| KR | 2016-0054997 A | 5/2016 |
| KR | 2016-0089551 A | 7/2016 |
| KR | 10-1692033 B1 | 1/2017 |
| MX | 2016006684 A | 9/2008 |
| WO | 2007/010975 | 1/2007 |
| WO | 2012-092463 A1 | 7/2012 |
| WO | 2015-075473 A1 | 5/2015 |
| WO | 2016-182235 A1 | 11/2016 |
| WO | 2017/039365 | 3/2017 |

OTHER PUBLICATIONS

Monsma, C. etal "Interrelationship of stearic acid content . . . " Lipids, vol. 28, pp. 539-547. (Year: 1993).*
Matsuo, T. et al "Dietary D-psicose, a C-3 epimer of D-fructose . . . "Asia Pacific J. Clin. Nutr., vol. 10, No. 3, pp. 233-237. (Year: 2001).*
Kallio, H. et al "Regioisomerism of triacylglycerls in lard, tallow . . . " J. Agric. Food Chem., vol. 49, pp. 3363-3369. (Year: 2001).*

(Continued)

*Primary Examiner* — Leigh C Maier
(74) *Attorney, Agent, or Firm* — Renner, Otto, Boiselle & Sklar, LLP

(57) ABSTRACT

The present application relates to an allulose-containing composition for promoting excretion of vegetable lipids from the body and a food comprising the composition of the present application and vegetable lipids.

2 Claims, 5 Drawing Sheets

(56) References Cited

OTHER PUBLICATIONS

Delamarre, S. et al. "The microbiology and historical safety of margarine" Food Microbiol., vol. 16, pp. 327-333. (Year: 1999).*
Masaru Ochiai et al., "Inhibition by dietary D-psicose of body fat accumulation in adult rats fed a high-sucroce diet", Biosci. Biotechnol. Biochem., 2013, 77(5), 1123-1126.
Yasuo Nagata et al., "D-Psicose, an epimer of D-fructose, favorably alters lipid metabolism in Sprague-Dawley rats", Journal of Agricultural and Food chemistry, 2015, 63, 3168-3176.
Han, Younji et al., "D-Allulose supplementation normalized the body weight and fat-pad mass in diet-induced obese miceh via the regulation of lipid metabolism under isocaloric fed condition", Molecular Nutrition&Food Research, Apr. 24, 2016, 60, 7, 1695-1706.
International Search Report and Written Opinion for corresponding Patent Application No. PCT/KR2017/015496 dated Mar. 29, 2018.
Itoh, et al., "Beneficial Effects of Supplementation of the Rare Sugar "D-allulose" Against Hepatic Steatosis and Severe Obesity in Lepob/Lepob Mice", Journal of Food Science, 2015, vol. 80, Nr. 7, H1619-H1626.
Han, Younji, "Effect of D-psicose on regulation of lipid and glucose metabolism with antioxidant profile in diet induced obese C57BL/6J mice", Thesis for the Degree of Master of Food science and Nutrition, The Graduate School of Kyungpook National University, 2015, 1-64.
Baek et al., "D-Psicose, a Sweet Monosaccharide, Ameliorate Hyperglycemia, and Dyslipidemia in C57BL/6J db/db Mice", Journal of Food Science, 2010, vol. 75, No. 2, pp. H49-H53, XP009511230.
Extended European Search Report for corresponding European Patent Application No. 17887817.9 dated Apr. 24, 2020.
Matsuo T. et al., "Dietary D-psicose, a C-3 epimer of D-fructose, suppresses the activity of hepatic lipogenic enzymes in rats", Asia Pacific Journal of Clinical Nutrition, 2001, vol. 10, No. 3, pp. 233-237.
Office Action issued by Singapore Patent Office for corresponding Singapore Patent Application No. 11201903370S dated Aug. 13, 2020.
Office Action dated Sep. 16, 2021 in corresponding Columbian Application No. 2019005180A.

* cited by examiner

[FIG. 1a]
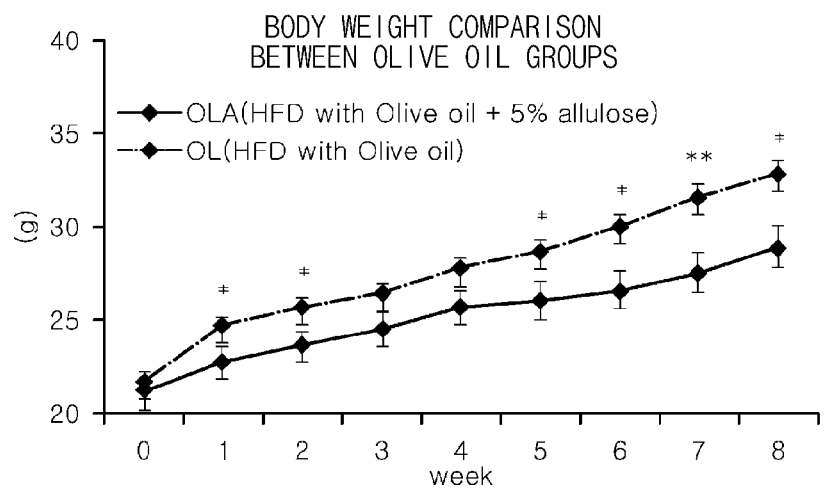
[FIG. 1b]
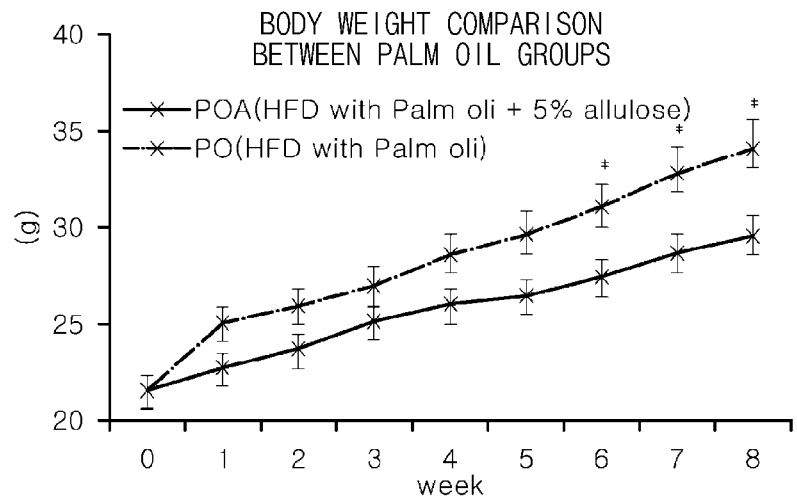

[FIG. 1c]
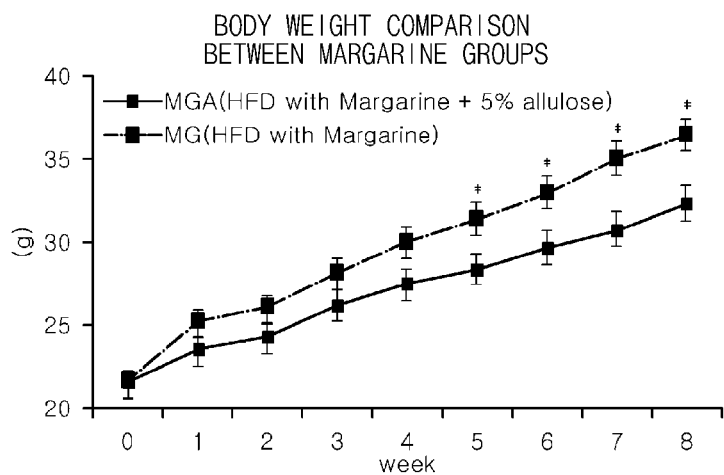
[FIG. 1d]
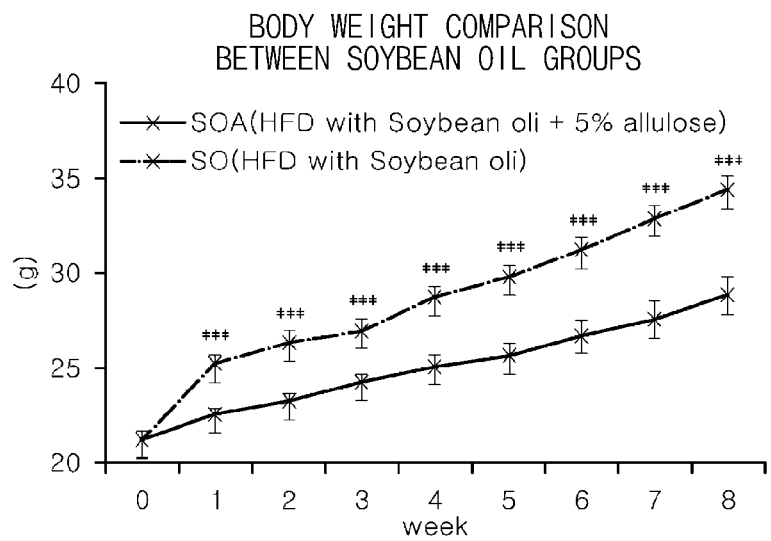

[FIG. 1e]
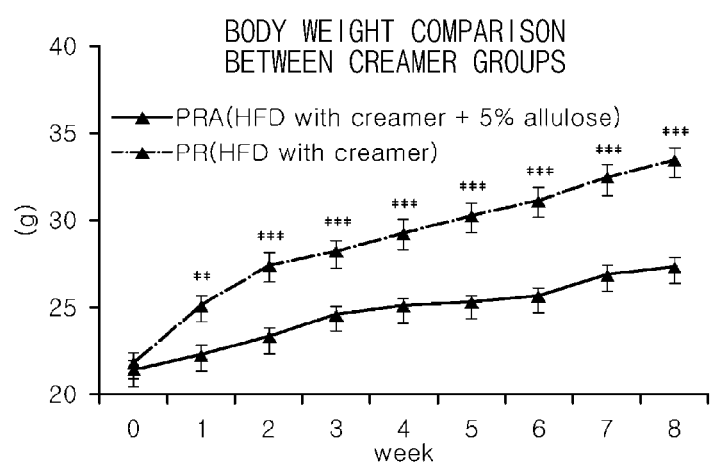

[FIG. 2a]
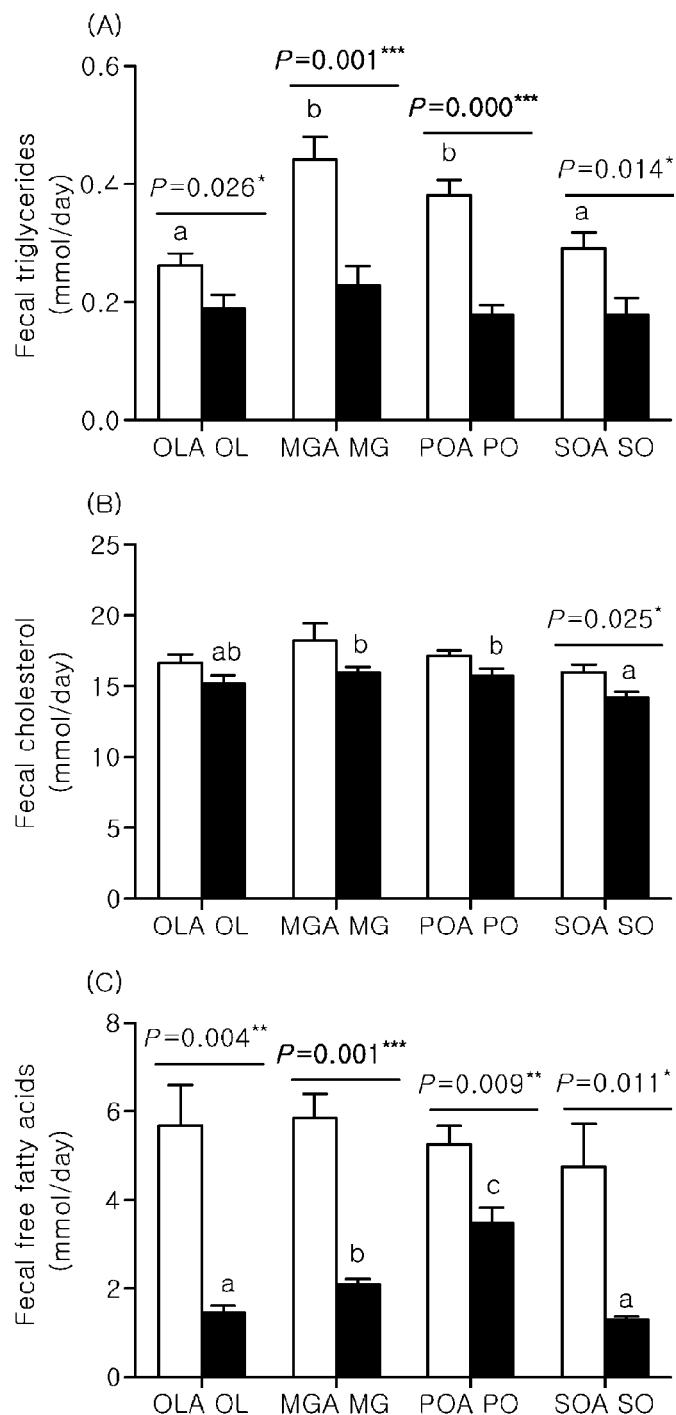

[FIG. 2b]
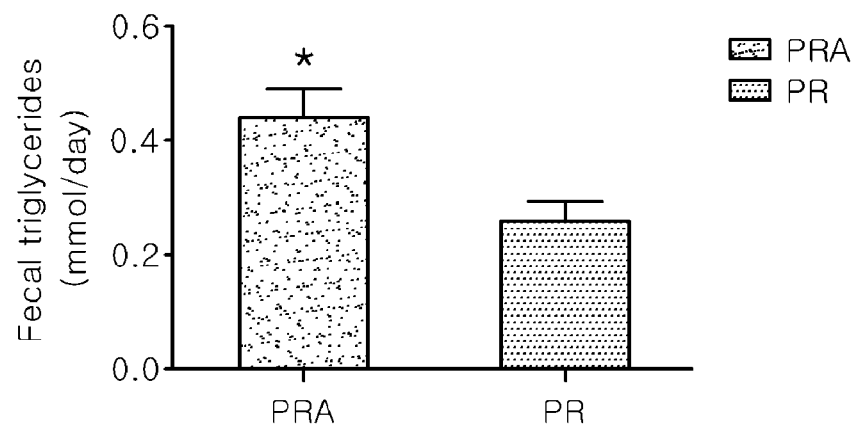
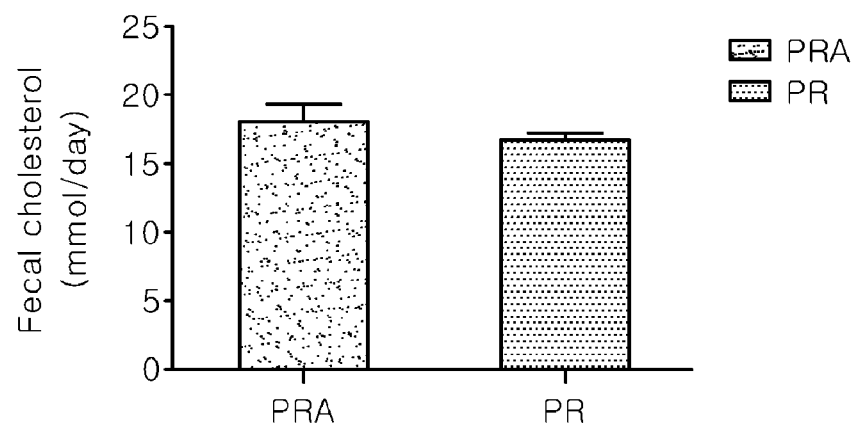
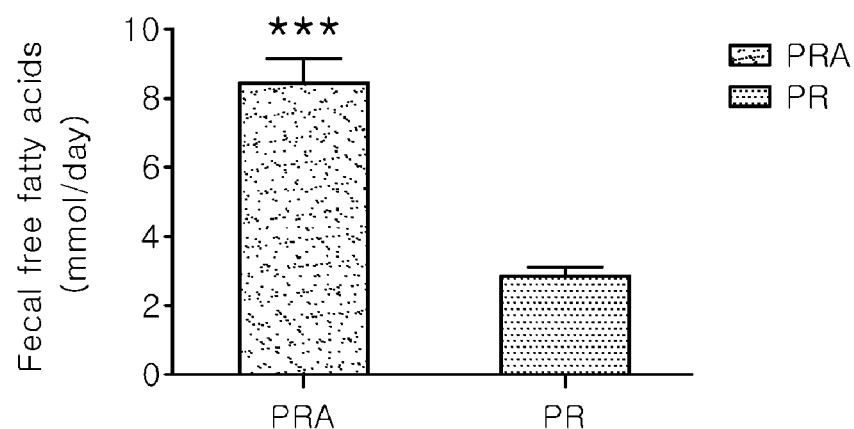

ALLULOSE-CONTAINING COMPOSITION FOR PROMOTING EXCRETION OF VEGETABLE LIPIDS FROM THE BODY

CROSS-REFERENCE TO RELATED APPLICATIONS

This application claims the benefit of Korean Patent Application No. 10-2016-0179487, filed on Dec. 26, 2016, and Korean Patent Application No. 10-2016-0179488, filed on Dec. 26, 2016 in the Korean Intellectual Property Office, the disclosures of which are incorporated herein in its entirety by reference.

TECHNICAL FIELD

The present application relates to an allulose-containing composition for promoting excretion of vegetable lipids from the body.

BACKGROUND ART

The recommended energy intake from lipids is 20-25% in Japan and 30% in the US and Europe (Edible fats and oils: Uses thereof and fat and oil foods, Naeha Corp., translated by Bonghyun, KIM). However, lipid consumption is increasing worldwide, and it has been reported that when high consumption of lipids is continued, the risks of obesity and various adult diseases and chronic diseases may increase.

Allulose (D-psicose), which is the C-3 epimer of D-fructose, is a natural sugar present in a trace amount in commercial mixtures of D-glucose and D-fructose obtained from the hydrolysis of sucrose or isomerization of D-glucose. It was determined to be generally recognized as safe (GRAS) by the United States Department of Agriculture (USDA). Since allulose is not metabolized in the human body so as to have little calories, but has 70% of the sweetness of sucrose, and thus, is a sweetener which can replace sucrose, it is currently under active development. A study reported that allulose affects lipid metabolism (Yasuo nagata et al., J. Agric, Food Chem. 2015, 63, 3168-3176), but an effect of excreting lipids from the body has not been reported.

Under these circumstances, the present inventors found that allulose has an excellent effect of fecal excretion of vegetable lipids, thereby completing the present application.

DISCLOSURE OF THE INVENTION

Technical Problem

An aspect of the present application provides an allulose-containing composition for promoting excretion of vegetable lipids from the body.

Another aspect of the present application provides a food comprising the composition of the present application and vegetable lipids.

Technical Solution

Hereinafter, the present application is described in more detail. The contents not described in this specification can be sufficiently recognized and inferred by those skilled in the art or similar fields of the present application, and thus, the description thereof will be omitted.

The respective explanations and embodiments disclosed in the present application can also be applied to other explanations and embodiments, respectively. That is, all combinations of various elements disclosed in this application fall within the scope of the present application. In addition, it could not be said that the scope of the present application is limited by the specific description to be described below.

In addition those skilled in the art will recognize and confirm many equivalents to specific aspects of the present application described in this application by using only routine experimentation. Such equivalents are also intended to be included in the present application.

According to an aspect of the present application, there is provided an allulose-containing composition for promoting excretion of vegetable lipids from the body.

The allulose used in the present application may be, but not limited to, one directly extracted from natural products or one produced by chemical synthesis or biological methods. In an embodiment, the allulose contained in a creamer of the present application may be liquid or crystalline allulose. Specifically, the allulose may be crystalline allulose and more specifically, the crystalline allulose may have a purity of 90% to 99.5%.

The vegetable lipids of the present application may be one or more selected from the group consisting of soybean oil, olive oil, palm oil, corn oil, palm olein oil, palm stearin oil, coconut oil, canola oil, and sunflower oil, and hydrogenated oils thereof.

In addition, in the present application, the excretion may be of triglycerides, cholesterol, free fatty acids, or a combination thereof. Specifically, the excretion of the present application may be fecal excretion.

The composition for promoting excretion of vegetable lipids from the body of the present application may be a pharmaceutical composition, a composition for a functional foods, or a food composition.

The composition of the present application may be administered orally or parenterally (e.g., intravenously, subcutaneously, intraperitoneally or topically) depending on the desired method, and specifically, may be administered orally.

When the composition of the present application is used as a pharmaceutical composition, it may further comprise one or more pharmaceutically acceptable carriers for administration, in addition to the allulose. As for the pharmaceutically acceptable carrier, saline solution, sterilized water, Ringer's solution, buffered saline, dextrose solution, maltodextrin solution, glycerol, and ethanol, and a mixture of one or more components selected therefrom may be used and in accordance with circumstances, other common additives such as antioxidants, buffer solutions, bacteriostatic agents, etc. may be added. Diluents, dispersants, surfactant, binders, and lubricants may also be additionally added to the composition of the present application, and the composition may be prepared into injectable formulations, such as aqueous solutions, suspensions or emulsions, pills, capsules, granules, or tablets. The composition of the present application may be prepared into various formulations depending on the type of disease or the kind of components according to any suitable method in the art or any of methods disclosed in Remington's Pharmaceutical Science (the newest edition), Mack Publishing Company, Easton Pa.

The dose ranges of the pharmaceutical composition of the present application vary depending on body weight, age, gender, the health condition of the patient, diet, time and mode of administration, the rate of excretion, the severity of the disease, etc. A daily dose of allulose of the present application may be from about 0.0001 to about 600 mg/kg, specifically about 0.001 to about 500 mg/kg, and may be administered in a single dose or multiple divided doses per day.

The pharmaceutical composition of the present application may be used alone or in combination with surgery, hormone therapy, drug therapy, and therapies using biological response modifiers.

The composition of the present application may be used as a food or a functional food composition. When the composition of the present application is used as the food or the functional food composition, the allulose may be added as it is or in combination with other foods or food ingredients and may be suitably used according to any common methods. The mixing amount of the active ingredient may be determined appropriately according to the purpose of use (prevention, health or therapeutic treatment). The food or functional food composition may be, without limitation, any food or functional food composition as long as it contains vegetable lipids. Examples of the food or functional food composition of the present application include meats, sausages, breads, cakes, chocolates, candies, snacks, confectionery (cookies, crackers, etc.), pizza, noodles (ramen, etc.), gums, dairy products including ice creams, various soups, ketchups, sauces, gravies, dressings, beverages, teas, drinks, alcoholic drinks, vitamin complexes, etc.

In addition to the above ingredients, the food or functional food composition of the present application may further contain a variety of nutritional supplements, vitamins, electrolytes, flavors, colorants, pectic acid and its salts, alginic acid and its salts, organic acids, protective colloidal thickeners, pH adjusting agents, stabilizers, preservatives, glycerin, alcohols, carbonating agents for carbonated beverages, etc. These ingredients may be used independently or in combination. The proportion of the additives may be selected from the range of 0.01 to 0.20 parts by weight, relative to 100 parts by weight of the food or functional food composition of the present application.

According to another aspect of the present application, there is provided a food comprising the composition of the present application and vegetable lipids. In addition, in the food of the present application, the allulose may be contained in an amount of 20 to 150 parts by weight based on 100 parts by weight of the vegetable lipids.

Specifically, the food of the present application may be margarine or creamer. More specifically, the margarine of the present application may further include one or more ingredients selected from the group consisting of water, sodium chloride, milk, lecithin, an organic acid, and an emulsifier. In addition, the creamer of the present application may further include casein, maltose, and phosphate. In addition, the creamer of the present application may be in powdered form, and specifically, may have a water content of from 0.5% to 5%. In an embodiment, the creamer of the present application may be coffee creamer or tea creamer.

In the food of the present application, the allulose may be contained in an amount of 20 to 150 parts by weight based on 100 parts by weight of the vegetable lipids. Specifically, the content of the allulose may be contained in an amount of 20 to 100 parts by weight, 20 to 50 parts by weight, 20 to 40 parts by weight, 30 to 150 parts by weight, 30 to 100 parts by weight, 30 to 50 parts by weight, or 30 to parts by weight, based on 100 parts by weight of the vegetable lipids.

In an embodiment, the food of the present application may not contain sugar.

In the food of the present application, the descriptions of the composition, the vegetable lipids, and the food are as described in the above-mentioned aspects.

Meanwhile, according to another aspect of the present application, there is provided a method for promoting excretion of vegetable lipids administered to a subject from the body, the method comprising a step of administering the vegetable lipids to the subject; and a step of administering allulose to the subject prior to, following, or simultaneously with the step of administering the vegetable lipids to the subject. The subject may be a human or an animal.

In the method of the present application, 20 to 150 parts by weight of the allulose may be administered based on 100 parts by weight of the vegetable lipids consumed by the subject. Specifically, 20 to 100 parts by weight, 20 to 50 parts by weight, 20 to 40 parts by weight, 30 to 150 parts by weight, 30 to 100 parts by weight, 30 to 50 parts by weight, or 30 to 40 parts by weight of the allulose may be administered based on 100 parts by weight of the vegetable lipids. The administration may be oral administration.

In the method of the present application, the descriptions of the allulose, the vegetable lipids, the administration, and the excretion are as described in the above-mentioned aspects.

According to another aspect of the present application, there is provided a use of an allulose-containing composition for promoting the excretion of vegetable lipids contained in a food.

In the use of the present application, the descriptions of the allulose, the food, the vegetable lipids, and the excretion are as described in the above-mentioned aspects.

Advantageous Effects

In the present application, the allulose provided along with vegetable lipids was found to remarkably increase fecal excretion of lipids. Accordingly, the present application has an effect of reducing consumer concerns regarding high consumption of lipids due to the ingestion of vegetable lipids or foods containing the same.

BRIEF DESCRIPTION OF THE DRAWINGS

FIG. 1 shows changes in the body weight observed in C57BL/6J mice fed with a high-fat diet (HFD) containing vegetable lipids along with allulose for 8 weeks. In FIGS. 1a to 1d, abbreviations for a control group represent as follows: OL: olive oil provision, MG: margarine provision, PO: palm oil provision, SO: soybean oil provision. In FIGS. 1a to 1d, abbreviations for a test group are as follows: OLA: olive oil+5% allulose provision, w/w, MGA: margarine+5% allulose provision, w/w, POA: palm oil+5% allulose provision, w/w, SOA: soybean oil+5% allulose provision, w/w.

Meanwhile, FIG. 1e shows changes in the body weight observed in C57BL/6J mice fed with a high-fat diet (HFD) containing creamer along with allulose for 8 weeks. Herein, PR for a control group represents the provision with a high-fat diet (HFD) along with creamer and PRA represents the provision with a high-fat diet (HFD)+creamer+5% allulose (w/w).

FIG. 2a shows changes in the fecal lipid excretion after 8 weeks observed in C57BL/6J mice fed with a high-fat diet (HFD) containing vegetable lipids along with allulose. Herein, data were represented as means±SE. Significance between the group without allulose and the group with 5% allulose is as follows: *$p<0.05$, $p<0.01$, *$p<0.001$. In FIG. 2a, each abbreviation represents as follows: OLA, HFD+olive oil+5% allulose (w/w); OL, HFD+olive oil; MGA, HFD+margarine+5% allulose (w/w); MG, HFD+ margarine; POA, HFD+palm oil+5% allulose (w/w); PO, HFD+palm oil; SOA, HFD+soybean oil+5% allulose (w/w); SO, HFD+soybean oil.

FIG. 2b shows changes in the fecal lipid excretion after 8 weeks observed in C57BL/6J mice fed with a high-fat diet (HFD) containing creamer along with allulose. Herein, data were represented as means±SE. Significance between the group without allulose and the group with 5% allulose is as follows: *p<0.05, p<0.01, *p<0.001. In FIG. 2, PRA represents "HFD+creamer+5% allulose (w/w)" and PR represents "creamer+HFD."

MODE FOR CARRYING OUT THE INVENTION

Hereinafter, preferred examples are presented to help an understanding of the present application. However, the following examples are provided for easier understanding of the present application, and the contents of the present application are not limited by examples.

Experimental Methods

1. Experimental Animal Breeding 1-1. Palm Oil, Olive Oil, Soybean Oil, and Margarine Twenty C57BL/6J mice (male, 4-week-old) were purchased from The Jackson Laboratory (USA) and used. After the animals were acclimated to the feeding environment with a lab-chow diet (Purina Co., USA) for 4 weeks, they were divided by a randomized block design into two groups: a negative control group without the ingestion of allulose (n=10/one kind of lipid); and a test group with the ingestion of allulose (n=10/one kind of lipid) and they were fed with the diets for 8 weeks.

For the negative control group, the high-fat diet was applied to the AIN-76 diet, and the vegetable lipids [palm oil (Wilmar, Malaysia), olive oil (CJ CheilJedang Corp., South Korea), soybean oil (CJ CheilJedang Corp., South Korea), margarine (Ottogi Foods Co., Ltd., 'Corn margarine', raw materials: consisted of 80 wt % of vegetable lipids (palm olein oil, palm stearin oil, coconut oil, corn oil)] were included. For the test group, among the ingredients of the diet for the negative control group, 5 wt % of sucrose was replaced with allulose (crystalline allulose, 98 wt % of allulose based on dry solids, CJ CheilJedang Corporation) (Table 1). All the animal experiments were carried out under the approval of the Ethics Committee for Animal Studies at Kyungpook National University, South Korea (approval no. KNU-2013-18).

[Table 1] Composition of test feed (% of diet, w/w)

TABLE 1

| Classification | Palm oil (PO) | Olive oil (OL) | Soybean oil (SO) | Margarine (MG) | POA | OLA | SOA | MGA |
|---|---|---|---|---|---|---|---|---|
| Casein | 20 | 20 | 20 | 20 | 20 | 20 | 20 | 20 |
| DL-Methionine | 0.3 | 0.3 | 0.3 | 0.3 | 0.3 | 0.3 | 0.3 | 0.3 |
| Corn starch | 11.1 | 11.1 | 11.1 | 11.1 | 11.1 | 11.1 | 11.1 | 11.1 |
| Sucrose | 37 | 37 | 37 | 37 | 32 | 32 | 32 | 32 |
| Cellulose | 5 | 5 | 5 | 5 | 5 | 5 | 5 | 5 |
| Palm oil | 14.6 | — | — | — | 14.6 | — | — | — |
| Olive oil | — | 14.6 | — | — | — | 14.6 | — | — |
| Soybean oil | — | — | 14.6 | — | — | — | 14.6 | — |
| Margarine | — | — | — | 14.6 | — | — | — | 14.6 |
| Lard | 5.4 | 5.4 | 5.4 | 5.4 | 5.4 | 5.4 | 5.4 | 5.4 |
| Mineral mix[1] | 4.2 | 4.2 | 4.2 | 4.2 | 4.2 | 4.2 | 4.2 | 4.2 |
| Vitamin mix[2] | 1.2 | 1.2 | 1.2 | 1.2 | 1.2 | 1.2 | 1.2 | 1.2 |
| Choline bitartrate | 0.2 | 0.2 | 0.2 | 0.2 | 0.2 | 0.2 | 0.2 | 0.2 |
| Cholesterol | 1 | 1 | 1 | 1 | 1 | 1 | 1 | 1 |
| tert-Butylhydroquinone | 0.004 | 0.004 | 0.004 | 0.004 | 0.004 | 0.004 | 0.004 | 0.004 |
| Allulose | — | — | — | — | 5 | 5 | 5 | 5 |
| Total (%) | 100 | 100 | 100 | 100 | 100 | 100 | 100 | 100 |
| kcal/g diet | 4.584 | 4.584 | 4.584 | 4.34 | 4.384 | 4.384 | 4.384 | 4.14 |

Note 1)
Mineral mix: AIN-76 mineral mixture (gram/kg): calcium phosphate, 500; sodium chloride, 74; potassium citrate, 2220; potassium sulfate, 52; magnesium oxide, 24; managanous carbonate, 3.5; ferric citrate, 6; zinc carbonate, 1.6; cupric carbonate, 0.3; potassium iodate, 0.01; sodium celenite, 0.01; chromium potassium sulfate, 0.55; sucrose 118.03

Note 2)
Vitamin mix: AIN-76 vitamin mixture (gram/kg): thiamin HCL, 0.6; riboflavin, 0.6; pyridoxine HCL, 0.7; nicotinic acid, 0.003; D-calcium pantothenate, 0.0016; folate, 0.2; D-biotin, 0.02; cyanocobalamin (vitamin B12), 0.001; retinyl palmitate premix, 0.8; DL-alpha tocopheryl acetate, premix, 20; cholecalciferol (vitamin D3), 0.0025; menaquinone (vitamin K), 0.05; antioxidant, 0.01; sucrose, finely powdered, 972.8

1-2. Creamer

Sixteen C57BL/6J mice (male, 4-week-old) were purchased from The Jackson Laboratory (USA) and used. After the animals were acclimated to the feeding environment with a lab-chow diet (Purina Co., USA) for 4 weeks, they were divided by a randomized block design into two groups: a negative control group without the ingestion of allulose (PR, n=8); and a test group with the ingestion of allulose (PRA, n=8) and they were fed with the diets for 8 weeks.

For the negative control group, the high-fat diet was applied to the AIN-76 diet, and as the vegetable lipid, creamer [Dongsuh foods corporation 'Prima', South Korea, raw materials: vegetable hydrogenated oil 30-38 wt % (coconut hydrogenated oil, palm hydrogenated oil), starch syrup (including maltose), sodium casein, potassium phosphate, dibasic, calcium phosphate, tribasic] was used. For the test group, among the ingredients of the diet for the negative control group, 5 wt % of sucrose was replaced with allulose (crystalline allulose, 98 wt % of allulose based on dry solids, CJ CheilJedang Corporation) (Table 2). All the animal experiments were carried out under the approval of the Ethics Committee for Animal Studies at Kyungpook National University, South Korea (approval no. KNU-2013-18).

[Table 2] Composition of test feed (% of diet, w/w)

TABLE 2

| Classification | Neg. Cont. Group (PR) | Test Group (PRA) |
|---|---|---|
| Casein | 20 | 20 |
| DL-Methionine | 0.3 | 0.3 |
| Corn starch | 11.1 | 11.1 |
| Socrose | 37 | 32 |
| Cellulose | 5 | 5 |
| Creamer(Prima) | 14.6 | 14.6 |
| Lard | 5.4 | 5.4 |
| Mineral mix[1] | 4.2 | 4.2 |
| Vitamin mix[2] | 1.2 | 1.2 |
| Choline bitartrate | 0.2 | 0.2 |
| Cholesterol | 1 | 1 |
| tert-Butylhydroquinone | 0.004 | 0.004 |
| Allulose | — | 5 |
| Total (%) | 100 | 100 |
| kcal/g diet | 4.047 | 4.847 |

Note
[1]Mineral mix: it is the same as in Table 1 above and thus will be omitted here.
Note
[2]Vitamin mix: it is the same as in Table 1 above and thus will be omitted here.

All groups were allowed to ingest the iso-energetic diet of the same level by pair feeding based on the test group so as to exclude the calorie-reducing effect due to the allulose and the diets were kept refrigerated at 4° C. during the feeding period. The animals were housed in an individual cage under constant temperature (25±2° C.), constant humidity (50±5%), and a 12 h dark-light cycle.

2. Measurement of Dietary Intake and Body Weight

Dietary intake was measured at a constant time every day, and the body weight was measured at a constant time every week.

3. Fecal Sample Collection and Analysis 3-1. Fecal Sample Collection

The feces were collected for 84 hours (3.5 days) after termination of the feeding, dried and then stored in the freezer.

3-2. Fecal Lipid Extraction

For the measurement, neutral lipid, cholesterol, and free fatty acids in the feces were extracted by modifying and supplementing the method of Folch et al. (1957). Specifically, the dried feces were ground in a mortar to take 0.5 g and then, 5 mL of a solution of chloroform:methanol (2:1, v/v) was added thereto, and the lipids were extracted at 4° C. for 24 hours. The extract was centrifuged at 3000×g (4° C.) for 10 minutes, and then 3 ml of the supernatant was taken out and dried under nitrogen gas at 37° C. and then dissolved again in 1 ml of the same extraction solvent. 200 μL of each sample for the measurement of neutral lipid, cholesterol, and free fatty acids was taken, dried again under nitrogen gas and the samples for the measurement of the neutral lipid and total cholesterol were dissolved in 500 μL of ethanol. The sample for the measurement of the free fatty acids was dissolved in 2.25 ml of NaOH and then 1 M HCl solution was added thereto to adjust the pH to the range of 2-3. To remove the turbidity occurring from the development with 3 mM cholic acid (sodium salt), 0.5% Triton X-100 as an emulsifier was mixed with an enzyme test solution during the quantification of total cholesterol and neutral lipids.

3-3. Quantification of Total Cholesterol in Feces

For the measurement of total cholesterol, 10 μL of a solution dissolved in 500 μL of ethanol and 690 μL of the emulsifier were mixed and 800 μL of a test solution for the measurement (kit, Asan pharmaceutical Co., Ltd.) to which the enzyme method of Allain et al. (1974) was applied was mixed therewith. For the quantification of both free cholesterol (FC) and ester-type cholesterol (CE) in the feces, CE was converted by cholesterol esterase into FC and fatty acids. Among them, FC was subjected to the reaction with cholesterol oxidase to convert into $\Delta^4$-cholestenone. The resulting product and H2O2 which is the substrate were subjected to the reaction with peroxidase, phenol, and 4-amino-antipyrine to obtain a color developing material and the absorbance was measured at 500 nm. Quantification was carried out by comparing the measured value with the cholesterol standard curve.

3-4. Quantification of Fecal Neutral Lipids

For the measurement of the neutral lipid, 10 μL of a solution dissolved in 500 μL of ethanol and 690 μL of the emulsifier were mixed and 800 μL of a test solution for the measurement (kit, Asan pharmaceutical Co., Ltd.) to which the enzyme method of McGowan et al. (1983) was applied was mixed therewith. The neutral lipid was degraded by lipoprotein lipase into glycerol and fatty acids. Of the degradation products, glycerol formed, by ATP and the action of glycerol kinase (GK), L-α-glycerol phosphate, which reacted with O2 and glycerophosphoxidase (GPO) to produce H2O2. Peroxidase and 4-amino-antipyrane were treated thereto to develop red color and then absorbance was measured at 550 nm and quantification was carried out by comparison with the glycerol standard curve.

3-5. Quantification of Fecal Free Fatty Acids

The concentration of free fatty acids was measured using a test solution for the measurement of free fatty acids (Non-esterified fatty acid; NEFA kit, Wako, Japan) according to the color development principle using an enzyme method. First, acyl-coenzyme A synthase was applied to plasma free fatty acid to produce acyl-CoA, AMP, and pyrophosphoric acid. Then, acyl-coenzyme A oxidase was added thereto to generate 2,3-trans-enoyl-CoA and hydrogen peroxide. Peroxidase, 4-aminoantipyrine, and N-ethyl-N-(2-hydroxy-3-sulfopropyl)-m-toluidine were treated thereto to develop red color and then absorbance was measured at 546 nm and quantification was carried out by comparison with the free fatty acid standard curve.

Experimental Results

1. Confirmation of the Effect of Inhibiting Body Weight Gain Due to Allulose 1-1. Palm Oil, Olive Oil, Soybean Oil, and Margarine At the time of the 0th week of the diet, the body weights of the negative control group and the test group were similar (Table 3), but after 8 weeks of the diet, the effect of inhibiting the body weight gain in the test group was confirmed compared to the negative control group (Table 4 and FIGS. 1a to 1d). Specifically, in the cases of the MGA group and the OLA group, from the 5th week of the diet, and in the case of the POA group, from the 6th week of the diet, the significant effect of inhibiting the body weight gain was confirmed compared to the negative control group (FIGS. 1a to 1c). Particularly, in the case of the SOA group, the effect of inhibiting the body weight gain was exhibited from the 1st week of the diet and thus the excellent effect of inhibiting the body weight gain was confirmed compared to other vegetable lipids (FIG. 1d).

TABLE 3

|  |  | Olive oil | Magarine | Palm oil | Soybean oil | p-value* (ANOVA) |
|---|---|---|---|---|---|---|
| Initial body weight | Without allulose | 21.81± 0.41 | 21.71± 0.60 | 21.56 ± 0.81 | 21.22± 0.43 | 0.899 |
|  | With allulose (5%) | 21.28± 0.43 | 21.57± 0.53 | 21.62± 0.68 | 21.23± 0.42 | 0.933 |
|  | p-value** (t-test) | 0.386 | 0.873 | 0.957 | 0.985 |  |

Data were represented as means ± SE.
*ANOVA is a comparative analysis among four groups.
**t-test is the comparison value between the HFD without allulose and the HFD containing 5 wt % allulose in each group.

TABLE 4

|  |  | Olive oil | Magarine | Palm oil | Soybean oil | p-value* (A-NOVA) |
|---|---|---|---|---|---|---|
| Body weight on 8th week | Without allulose | 32.86± 0.66 | 36.47± 0.94 | 34.12± 1.44 | 34.39± 0.69 | 0.101 |
|  | With allulose (5%) | 28.87± 1.23# | 32.30± 1.16# | 29.57± 1.05# | 28.84± 0.95### | 0.115 |
|  | p-value** (t-test) | 0.014 | 0.016 | 0.025 | 0.001 |  |

Data were represented as means ± SE.
*ANOVA is a comparative analysis among four groups.
**t-test is the comparison value between the HFD without allulose and the HFD containing 5 wt % allulose in each group (#$p < 0.05$, ###$p < 0.001$).

1-2. Creamer

At the time of the 0th week of the diet, the body weights of the negative control group (PR) and the test group (PRA) were similar (Table 5). However, the body weight of the negative control group increased significantly from 1 week, whereas the body weight of the test group was remarkably inhibited from the 1st week of the diet and thus after 8 weeks of the diet, the significant effect of inhibiting the body weight gain in the test group was confirmed (Table 5 and FIG. 1e).

TABLE 5

|  |  | Without allulose (PR) | With allulose (PRA) | p-value** (t-test) |
|---|---|---|---|---|
| Body weight | 0 week | 21.93 ± 0.46 | 21.47 ± 0.50 | 0.517 |
|  | 8th week | 33.50 ± 0.69 | 27.41 ± 0.48 | 0.000 |

Data were represented as means ± SE.
**t-test is the comparison value between PR without allulose and PRA containing 5 wt % allulose in each group.

2. Confirmation of the Effect of Excreting Vegetable Lipids Due to Allulose 2-1. Palm Oil, Olive Oil, Soybean Oil, and Margarine The effect of excreting vegetable lipids due to allulose was confirmed by the lipid excretion in the feces.

As a result, it was confirmed that the contents of triglycerides and free fatty acids in the feces were significantly increased in the test groups of all kinds of oils compared to the negative control group. Particularly, it was confirmed that the contents of free fatty acids in the test groups were significantly higher than that in the negative control group (Tables 6 to 9 and FIGS. 2a (A) and (C)). In addition, it was confirmed that the SOA group also showed a significant increase in the cholesterol content in the feces compared to the SO group (FIG. 2a (B)).

TABLE 6

|  | OLA | OL |
|---|---|---|
| Triglycerides (mmol/day) | 0.26 ± 0.022* | 0.19 ± 0.022 |
| Cholesterol (mmol/day) | 16.56 ± 0.61 | 15.19 ± 0.54 |
| Free Fatty Acids (mmol/day) | 5.67 ± 0.93** | 1.50 ± 0.13 |

Data were represented as means ± SE. There was a significant difference between OLA and OL: *$p < 0.05$, **$p < 0.01$. OLA, HFD + olive oil + 5% allulose; OL, HFD + olive oil.

TABLE 7

|  | MGA | MG |
|---|---|---|
| Triglycerides (mmol/day) | 0.44 ± 0.038*** | 0.23 ± 0.031 |
| Cholesterol (mmol/day) | 18.20 ± 1.16 | 16.00 ± 0.35 |
| Free Fatty Acids (mmol/day) | 5.83 ± 0.57*** | 2.11 ± 0.10 |

Data were represented as means ± SE. There was a significant difference between MGA and MG:
***$p < 0.001$.
MGA, HFD + margarine + 5% allulose; MG, HFD + margarine.

TABLE 8

|  | POA | PO |
|---|---|---|
| Triglycerides (mmol/day) | 0.38 ± 0.026*** | 0.18 ± 0.013 |
| Cholesterol (mmol/day) | 17.07 ± 0.42 | 15.68 ± 0.54 |
| Free Fatty Acids (mmol/day) | 5.22 ± 0.45** | 3.50 ± 0.32 |

Data were represented as means ± SE. There was a significant difference between POA and PO:
**$p < 0.01$,
***$p < 0.001$.
POA, HFD + palm oil + 5% allulose; PO, HFD + palm oil.

TABLE 9

|  | SOA | SO |
|---|---|---|
| Triglycerides (mmol/day) | 0.29 ± 0.028* | 0.18 ± 0.027 |
| Cholesterol (mmol/day) | 15.92 ± 0.57* | 14.19 ± 0.37 |
| Free Fatty Acids (mmol/day) | 4.76 ± 0.95* | 1.29 ± 0.054 |

Data were represented as means ± SE. There was a significant difference between SOA and SO:
*$p < 0.05$.
SOA, HFD + soybean oil + 5% allulose; SO, HFD + soybean oil.

2-2. Creamer

The effect of excreting lipids in the creamer due to allulose was confirmed by the lipid excretion in the feces.

As a result, it was confirmed that the contents of triglycerides and free fatty acids in the feces were significantly increased in the test group compared to the negative control group. Particularly, it was confirmed that the content of free fatty acids in the test group was significantly higher than that in the negative control group (Tables 10 and FIG. 2b).

TABLE 10

|  | PRA | PR |
| --- | --- | --- |
| Triglycerides (mmol/day) | 0.44 ± 0.053* | 0.26 ± 0.032 |
| Cholesterol (mmol/day) | 18.28 ± 0.97 | 16.81 ± 0.52 |
| Free Fatty Acids (mmol/day) | 8.39 ± 0.75*** | 2.78 ± 0.30 |

Data were represented as means ± SE. There was a significant difference between PR and PRA:
*$p < 0.05$,
***$p < 0.001$.
PRA, HFD + creamer + 5% allulose; PR, HFD + creamer 2-3. Consideration It was confirmed that when allulose was consumed along with vegetable lipids in the creamer, the fecal excretion of lipids was promoted. In addition, it was confirmed that when allulose was consumed along with each of palm oil, olive oil, soybean oil, and margarine, the fecal excretion of lipids was also promoted. Especially, when allulose was taken together with soybean oil, the effect of excreting lipids was excellent compared to the ingestion of allulose along with other vegetable lipids and the excretion of cholesterol was also increased.

The above-mentioned description of the present application is intended to be merely exemplary, and it will be understood by those skilled in the art to which the present application belongs that the present application can be easily modified into other specific forms without changing the technical concepts or essential features thereof. It is, therefore, to be understood that the above-described embodiments are illustrative in all aspects and not restrictive.

The invention claimed is:

1. A margarine composition comprising allulose and vegetable oils in an emulsion form,
the margarine composition made by a process comprising the steps of:
providing an amount of the vegetable oils, wherein the vegetable oils comprise corn oil, palm olein oil, palm stearin oil and coconut oil, and
combining the amount of the vegetable oils with an amount of the allulose that is 30 to 50 parts by weigh based on 100 parts by weight of the amount of vegetable oils, based on dry solids.

2. The margarine composition of claim 1, further comprising one or more ingredients selected from the group consisting of sodium chloride, milk, lecithin, and an organic acid.

* * * * *